(12) United States Patent
Fu et al.

(10) Patent No.: US 11,654,052 B2
(45) Date of Patent: May 23, 2023

(54) HIGH SPEED CORNEAL LENTICULAR INCISION USING A FEMTOSECOND LASER

(71) Applicant: AMO DEVELOPMENT, LLC, Irvine, CA (US)

(72) Inventors: Hong Fu, Pleasanton, CA (US); Alireza Malek Tabrizi, Fremont, CA (US); Nima Khatibzadeh, San Jose, CA (US)

(73) Assignee: AMO Development, LLC, Irvine, CA (US)

( * ) Notice: Subject to any disclaimer, the term of this patent is extended or adjusted under 35 U.S.C. 154(b) by 277 days.

(21) Appl. No.: 17/095,722

(22) Filed: Nov. 11, 2020

(65) Prior Publication Data

US 2021/0128358 A1    May 6, 2021

Related U.S. Application Data

(63) Continuation of application No. 16/057,740, filed on Aug. 7, 2018, now Pat. No. 10,842,674.

(51) Int. Cl.
*A61F 9/008* (2006.01)
*A61B 18/20* (2006.01)

(52) U.S. Cl.
CPC ...... *A61F 9/00804* (2013.01); *A61F 9/00814* (2013.01); *A61B 2018/20353* (2017.05); *A61B 2018/20553* (2017.05); *A61B 2018/205547* (2017.05); *A61F 9/00827* (2013.01); *A61F 2009/0087* (2013.01); *A61F 2009/00897* (2013.01)

(58) Field of Classification Search
CPC .. A61F 9/008; A61F 9/00802; A61F 9/00804; A61F 9/00814; A61F 9/00825; A61F 9/00827; A61F 9/00829; A61F 9/00836; A61F 9/0084; A61F 2009/0087; A61F 2009/00872; A61F 2009/00878; A61F 2009/00897
See application file for complete search history.

(56) References Cited

U.S. PATENT DOCUMENTS

| | | |
|---|---|---|
| 4,764,930 A | 8/1988 | Bille et al. |
| 5,993,438 A | 11/1999 | Juhasz et al. |

(Continued)

FOREIGN PATENT DOCUMENTS

| | | |
|---|---|---|
| WO | 2013077951 A1 | 5/2013 |
| WO | 2016137560 A1 | 9/2016 |

*Primary Examiner* — Eugene T Wu
(74) *Attorney, Agent, or Firm* — Johnson & Johnson Surgical Vision, Inc.

(57) ABSTRACT

An ophthalmic surgical laser system and method for forming a lenticule in a subject's eye using "fast-scan-slow-sweep" scanning scheme. A high frequency scanner forms a fast scan line, which is placed by the XY and Z scanners at a location tangential to a parallel of latitude of the surface of the lenticule. The XY and Z scanners then move the scan line in a slow sweep trajectory along a meridian of longitude of the surface of the lenticule in one sweep. Multiple sweeps are performed along different meridians to form the entire lenticule surface, and a prism is used to change the orientation of the scan line of the high frequency scanner between successive sweeps. In each sweep, the sweeping speed along the meridian is variable, being the slowest at the edge of the lenticule and the fastest near the apex.

15 Claims, 10 Drawing Sheets

(56) References Cited

U.S. PATENT DOCUMENTS

| | | | |
|---|---|---|---|
| 6,110,166 | A | 8/2000 | Juhasz |
| 6,315,413 | B1 | 11/2001 | Shimmick et al. |
| 8,260,024 | B2 | 9/2012 | Farrer et al. |
| 2011/0022036 | A1 | 1/2011 | Frey et al. |
| 2011/0172649 | A1 | 7/2011 | Schuele et al. |
| 2013/0281992 | A1 | 10/2013 | Seiler et al. |
| 2016/0089270 | A1 | 3/2016 | Fu |
| 2016/0250071 | A1 | 9/2016 | Horvath et al. |
| 2016/0374857 | A1* | 12/2016 | Fu ................... A61F 9/0084 606/3 |
| 2019/0110926 | A1 | 4/2019 | Malek et al. |

* cited by examiner

HIGH SPEED CORNEAL LENTICULAR INCISION USING A FEMTOSECOND LASER

This application claims priority to and is a continuation of U.S. patent application Ser. No. 16/057,740, filed Aug. 7, 2018, which is incorporated herein by reference in its entirety.

BACKGROUND OF THE INVENTION

Field of the Invention

Embodiments of this invention relate generally to laser-assisted ophthalmic procedures, and more particularly, to systems and methods for lenticular incisions in the cornea.

Description of Related Art

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

Prior surgical approaches for reshaping the cornea include laser assisted in situ keratomileusis (hereinafter "LASIK"), photorefractive keratectomy (hereinafter "PRK") and Small Incision Lens Extraction (hereinafter "SmILE").

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure.

In the SmILE procedure, instead of ablating corneal tissue with an excimer laser following the creation of a corneal flap, the technique involves tissue removal with two femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision.

SUMMARY OF THE INVENTION

Embodiments of the present invention provide a lenticular incision method using a pulsed laser which can reduce unnecessary laser energy exposure in the center area of the patient's field of view and reduce the time required for forming the incision.

In one aspect, embodiments of the present invention provides an ophthalmic surgical laser system which includes: a laser delivery system for delivering a pulsed laser beam to a target in a subject's eye; a high frequency scanner to scan the pulsed laser beam back and forth at a predefined frequency; an XY-scanner to deflect the pulsed laser beam, the XY-scanner being separate from the high frequency scanner; a Z-scanner to modify a depth of a focus of the pulsed laser beam; and a controller configured to control the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, wherein each sweep is formed by: controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex, and controlling the XY-scanner and the Z-scanner to move the scan line along a meridian of longitude of the lens, the meridian of longitude being a curve that passes through the apex and has a defined angular position around the Z axis, wherein a sweeping speed of moving the scan line along the meridian of longitude varies with a position of the scan line along the meridian of longitude, wherein the sweeping speed is higher when the scan line passes through the apex than when the scan line is at an edge of the lenticular incision, wherein the plurality of sweeps are successively formed one after another along the respective meridians of longitude which are different from one another.

In another aspect, embodiments of the present invention provide a method for creating a lenticular incision using an ophthalmic surgical laser system, the method including the steps of: generating a pulsed laser beam; delivering the pulsed laser beam to a target in a subject's eye; scanning, by a high frequency scanner, the pulsed laser beam back and forth at a predefined frequency; deflecting, by an XY-scanner, the pulsed laser beam, the XY-scanner being separate from the high frequency scanner; modifying, by a Z-scanner, a depth of a focus of the pulsed laser beam; and controlling, by a controller, the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, including forming each sweep by: controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex, and controlling the XY-scanner and the Z-scanner to move the scan line along a meridian of longitude of the lens, the meridian of longitude being a curve that passes through the apex and has a defined angular position around the Z axis, wherein a sweeping speed of moving the scan line along the meridian of longitude varies with a position of the scan line along the meridian of longitude, wherein the sweeping speed is higher when the scan line passes through the apex than when the scan line is at an edge of the lenticular incision, wherein the plurality of sweeps are successively formed one after another along the respective meridians of longitude which are different from one another.

In some embodiments, the sweeping speed is $$V(r) = V_{max} - \left(\frac{r}{R}\right)^2 * (V_{max} - V_{min})$$

where r is a distance of the scan line from the Z axis, R is a lateral radius of the lenticular incision, V(r) is the sweeping speed of the scan line as a function of r, $V_{max}$ is a first speed, and $V_{min}$ is a second speed, where $V_{max} > V_{min}$.

In another aspect, the present invention provides an ophthalmic surgical laser system which includes: a laser delivery system for delivering a pulsed laser beam to a target in a subject's eye; a high frequency scanner to scan the pulsed laser beam back and forth at a predefined frequency; an XY-scanner to deflect the pulsed laser beam, the XY-scanner being separate from the high frequency scanner; a Z-scanner to modify a depth of a focus of the pulsed laser beam; and a controller configured to control the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, wherein each sweep is formed by: controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex, controlling the XY-scanner and the Z-scanner to move the scan line along a meridian of longitude of the lens, the meridian of longitude being a curve that passes through the apex and has a defined angular position around the Z axis, and controlling the laser delivery system to vary a laser pulse energy during each sweep to use a lower laser pulse energy when the scan line is located within a vicinity of the apex of the lenticule than when the scan line is located at an edge of the lenticule, wherein the plurality of sweeps are successively formed one after another along the respective meridians of longitude which are different from one another.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF PREFERRED EMBODIMENTS

Embodiments of this invention are generally directed to systems and methods for laser-assisted ophthalmic procedures, and more particularly, to systems and methods for corneal lenticule incision.

Figure 1:
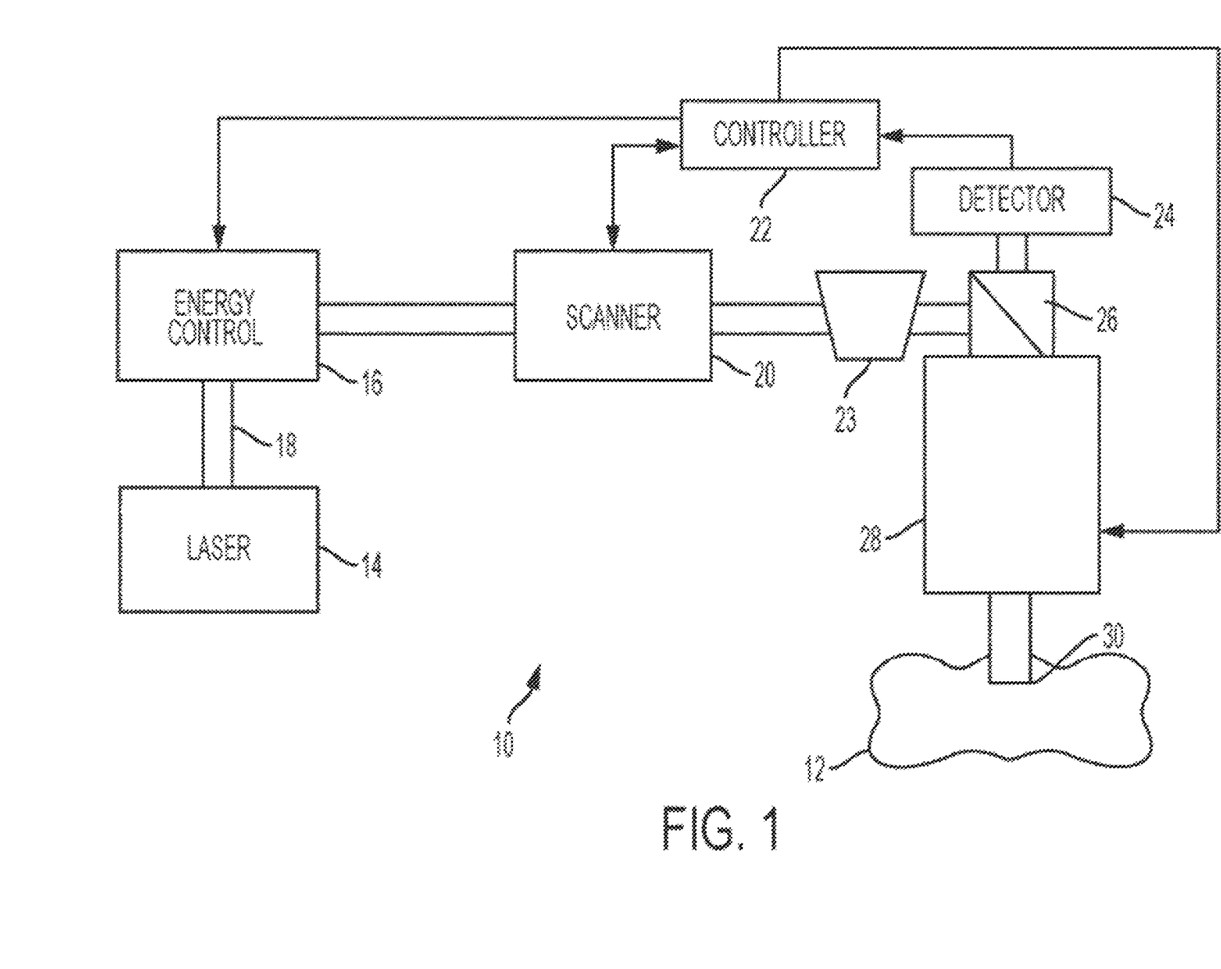
FIG. 1 is a perspective view of a surgical ophthalmic laser system which may be used to perform a lenticule incision method according to an embodiment of the present invention.

Referring to the drawings, FIG. 1 shows a system 10 for making an incision in a material 12. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor operating suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting or incision in response to the feedback, and may also modify the planned sculpting or incision based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 2:
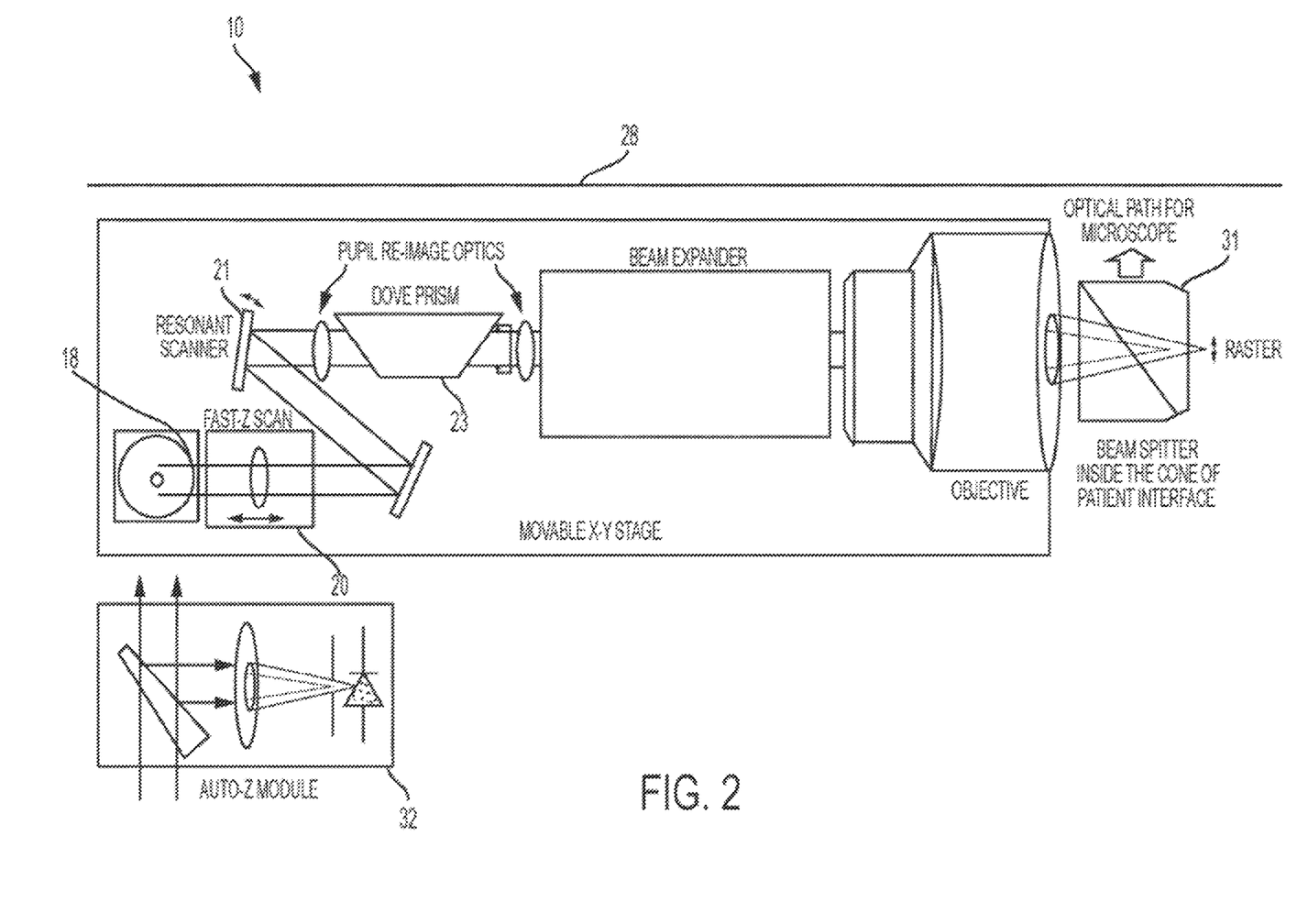
FIG. 2 is another perspective view of a surgical ophthalmic laser system which may be used to perform a lenticule incision method according to an embodiment of the present invention.

FIG. 2 shows another exemplary diagram of the laser system 10. FIG. 2 shows components of a laser delivery system including a moveable XY-scanner (or XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 50-100 nJ range and pulse repetitive rates (or "rep rates") in the 5-20 MHz range. A fast-Z scanner 20 and a resonant scanner 21 direct the laser beam 18 to the prism 23. When used in an ophthalmic procedure, the system 10 also includes a patient interface 31 design that has a fixed cone nose and a portion that engages with the patient's eye. A beam splitter is placed inside the cone of the patient interface to allow the whole eye to be imaged via visualization optics. In one embodiment, the system 10 uses: optics with a 0.6 numerical aperture (NA) which would produce 1.1 µm Full Width at Half Maximum (FWHM) focus spot size; and a resonant scanner 21 that produces 1-2 mm scan line with the XY-scanner scanning the resonant scan line to a 1.0 mm field. The prism 23 rotates the resonant scan line in any direction on the XY plane. The fast-Z scanner 20 sets the incision depth and produces a side cut. The system 10 may also include an auto-Z module 32 to provide depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

Figure 3:
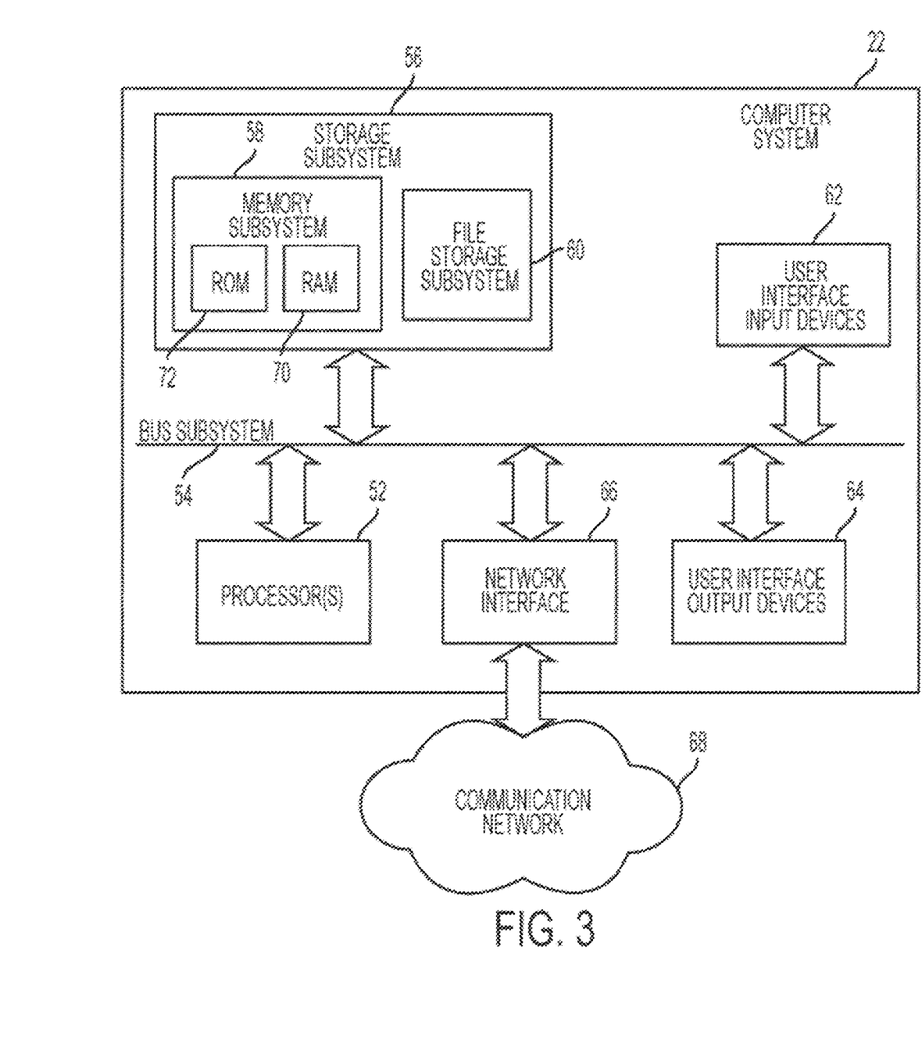
FIG. 3 is a simplified diagram of a controller of a surgical ophthalmic laser system which may be used to perform a lenticule incision method according to an embodiment of the present invention.

FIG. 3 illustrates a simplified block diagram of an exemplary controller 22 that may be used by the laser system 10 according to an embodiment of this invention to control the laser system 10 and execute at least some of the steps discussed in detail below. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 3 is intended only as an example for purposes of illustrating only one embodiment of the present invention. Many other configurations of controller 22, having more or fewer components than those depicted in FIG. 3, are possible.

As should be understood by those of skill in the art, additional components and subsystems may be included with laser system 10. For example, spatial and/or temporal integrators may be included to control the distribution of energy within the laser beam. Ablation effluent evacuators/filters, aspirators, and other ancillary components of the surgical laser system are known in the art, and may be included in the system. In addition, an imaging device or system may be used to guide the laser beam.

In an embodiment, the laser surgery system 10 includes a femtosecond oscillator-based laser operating in the MHz range, for example, 10 MHz, for example, from several MHz to tens of MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line. This is otherwise referred to as point-to-point scanning.

Figure 4:
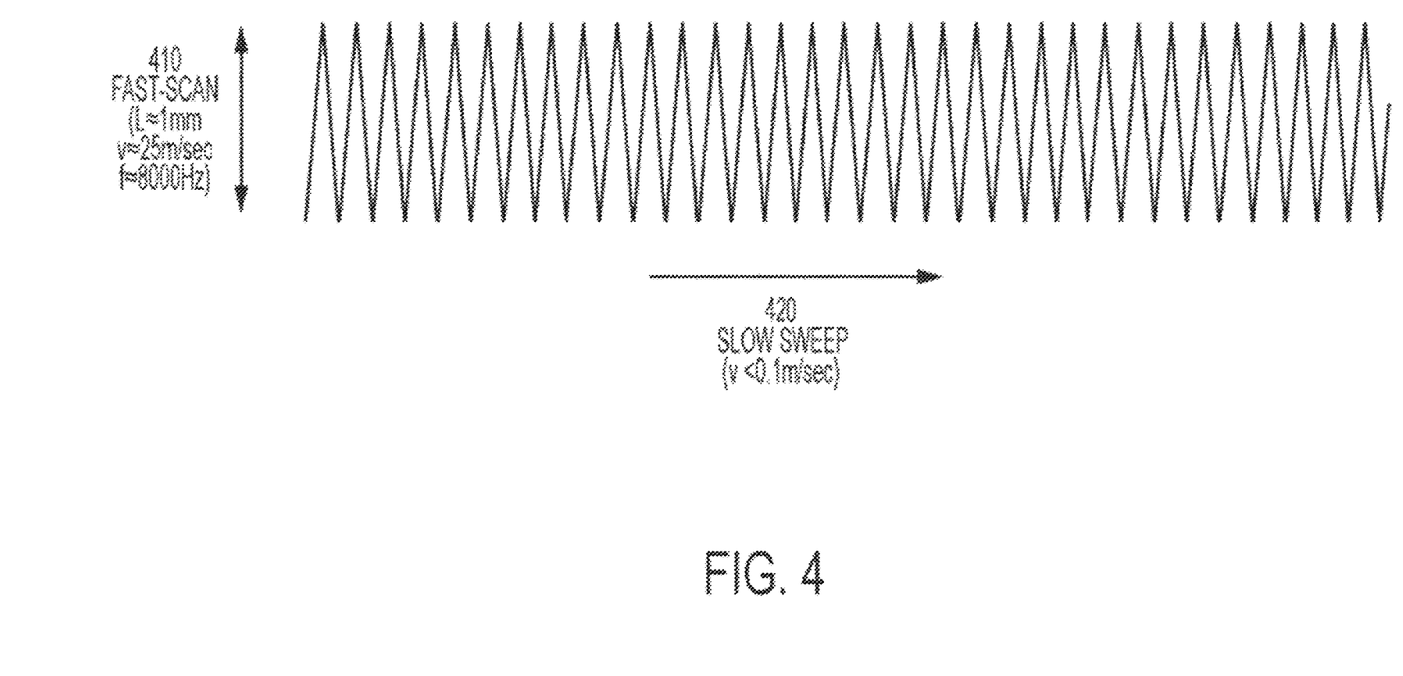
FIG. 4 illustrates an exemplary scanning of a surgical ophthalmic laser system according to an embodiment of the present invention.

In other embodiments, the beam scanning can be realized with a "fast-scan-slow-sweep" scanning scheme, also referred herein as a fast-scan line scheme. The scheme consists of two scanning mechanisms: first, a high frequency fast scanner is used to scan the beam back and forth to produce a short, fast scan line (e.g., a resonant scanner 21 of FIG. 2); second, the fast scan line is slowly swept by much slower X, Y, and Z scan mechanisms. FIG. 4 illustrates a scanning example of a laser system 10 using an 8 kHz (e.g. between 7 kHz and 9 kHz) resonant scanner 21 to produce a fast scan line 410 of about 1 mm (e.g., between 0.9 mm and 1.1 mm) and a scan speed of about 25 m/sec, and X, Y, and Z scan mechanisms with the scan speed (sweep speed) smaller than about 0.1 m/sec, or a variable sweep speed as described in more detail later. The fast scan line 410 may be perpendicular to the optical beam propagation direction, i.e., it is always parallel to the XY plane. The trajectory of the slow sweep 420 can be any three dimensional curve drawn by the X, Y, and Z scanning devices (e.g., XY-scanner 28 and Z-scanner 20). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 5:
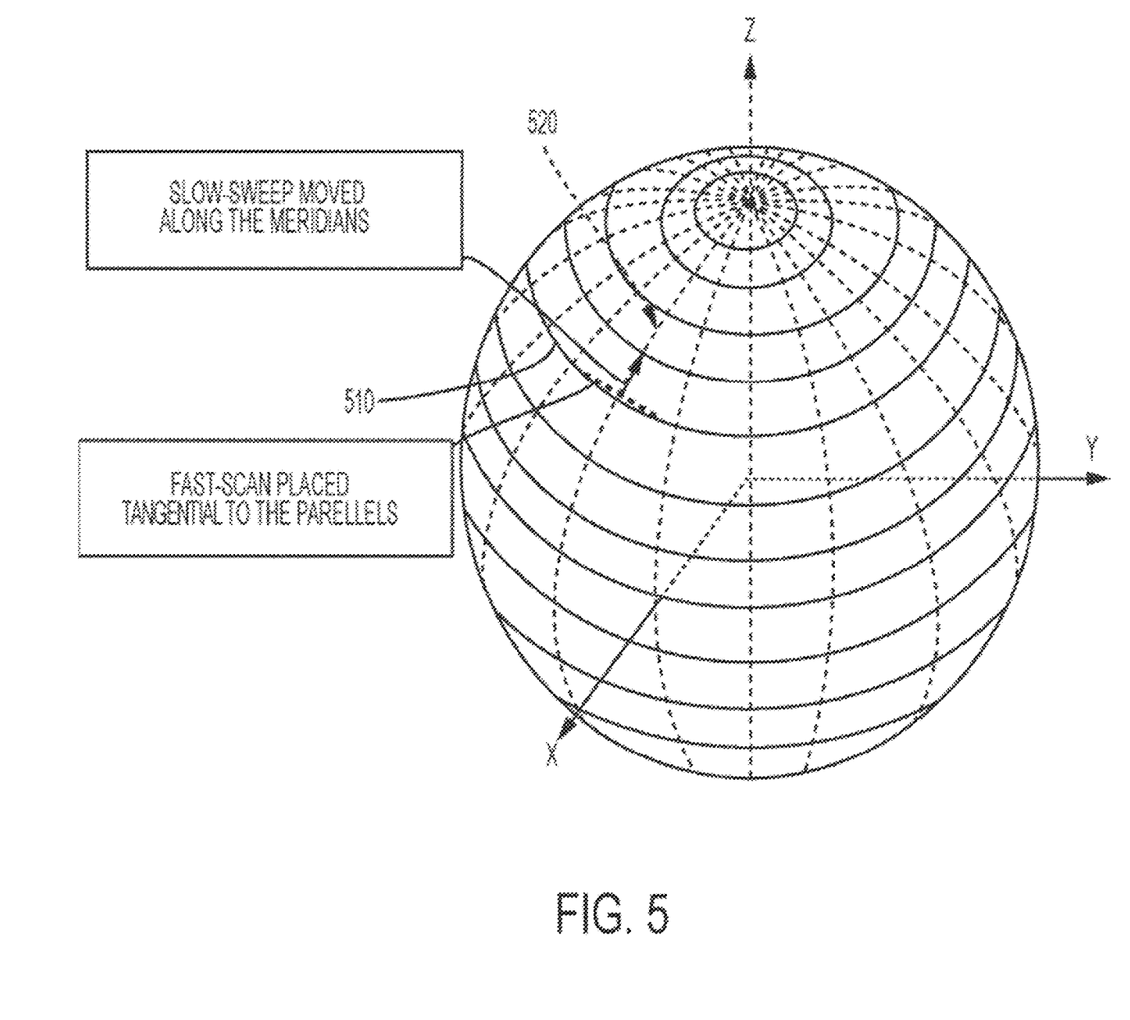
FIG. 5 illustrates an exemplary surface dissection using a fast-scan-slow-sweep scheme of a surgical ophthalmic laser system according to an embodiment of the present invention.
Figure 7:
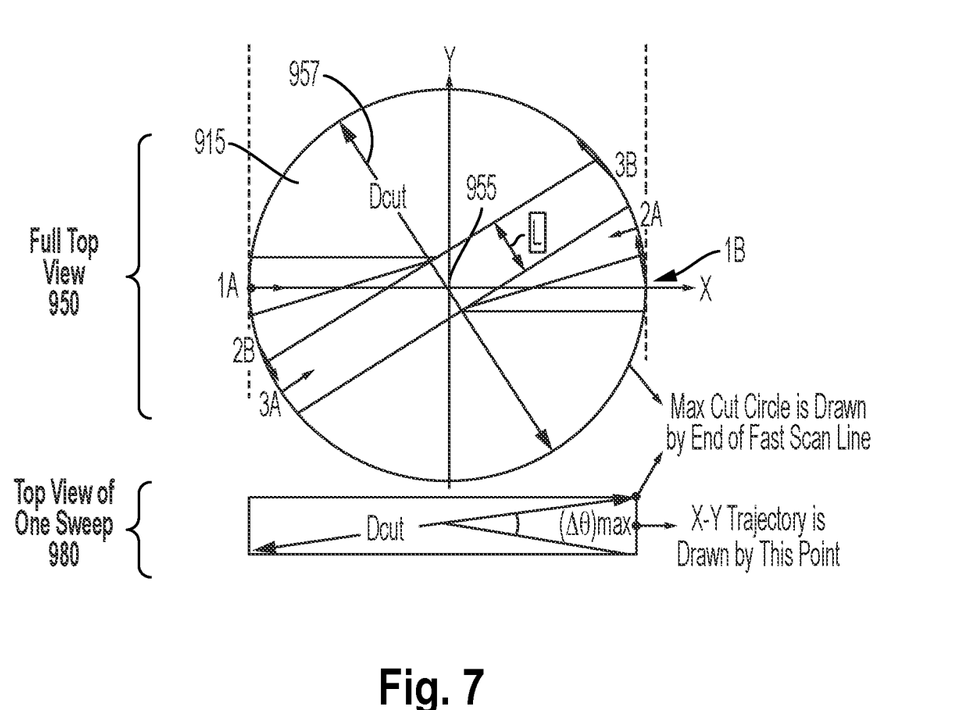
FIG. 7 illustrates an exemplary lenticular incision using a surgical ophthalmic laser system according to an embodiment of the present invention.

In a preferred embodiment shown in FIGS. 5 and 7A-7B, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 510 on the surface of the lenticule. A parallel of latitude is the intersection of the surface with a plane perpendicular to the Z axis (which is the axis parallel to the depth direction of the eye), i.e. a circle on the surface of the lens that is perpendicular to the Z axis and has a defined distance to the apex (the highest point in the Z direction). For example, in the miniaturized flap maker laser system 10 of FIG. 2, this can be realized by adjusting a prism 23 to the corresponding orientations via software, e.g., via the controller 22. Second, the slow sweep trajectory preferably moves along the meridians of longitude 520 on the surface of the lenticule. A meridian of longitude is the intersection of the surface with a plane that passes through the Z axis, i.e. a curve that passes through the apex and has a defined angular direction with respect to the Z axis. For example, in the miniaturized flap maker system of FIG. 2, this can be done by coordinating the XY scanner 28, and the Fast-Z scanner 20 via the software, e.g., via the controller 22. The procedure starts with the scan line being parallel to the XY plane, and sweeps through the apex of the lens, following the curvature with the largest diameter (see also FIG. 7A). Multiple sweeps are performed at successive angular directions with respect to the Z axis, for example as realized by rotating the prism 23 because successive sweeps, to form the entire lenticule. With this preferred procedure, there are no vertical "steps" in the dissection, and vertical side cuts are eliminated. As will be analyzed herein below, the deviations between the laser focus locations and the intended spherical surface dissections are also minimized.

Figure 6:
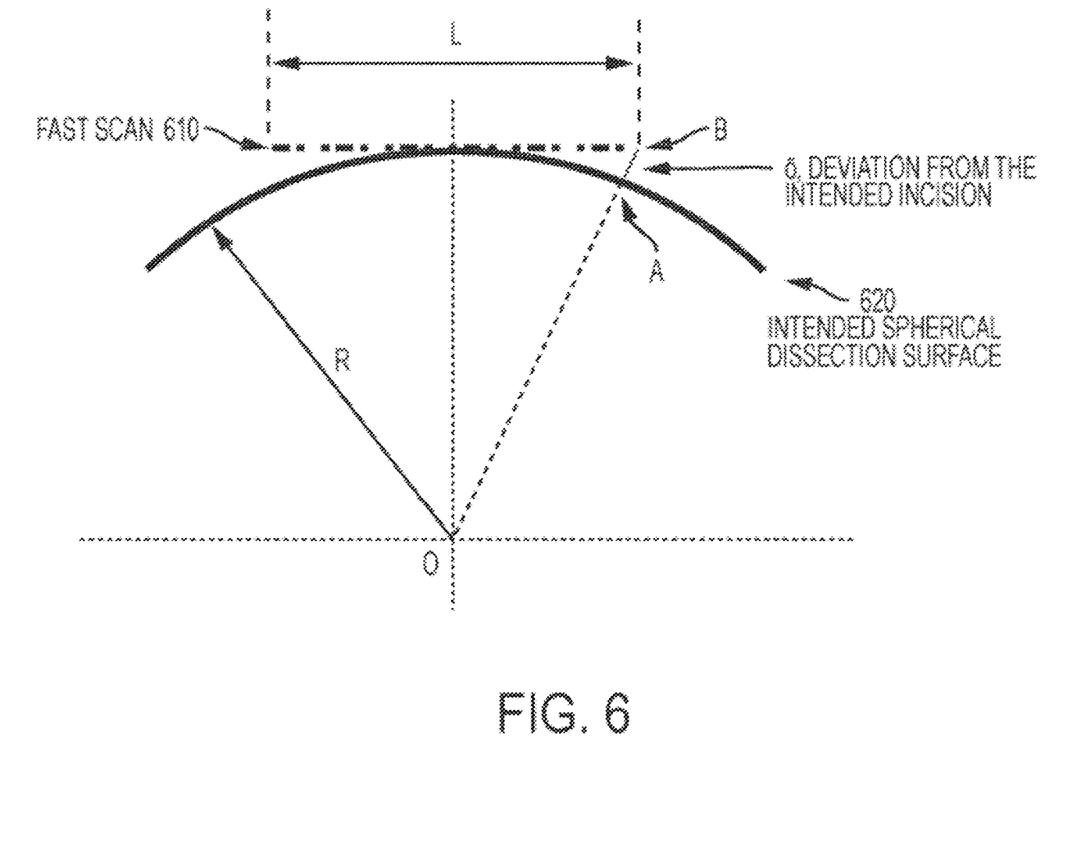
FIG. 6 illustrates a geometric relation between a fast-scan line and an intended spherical dissection surface of a surgical ophthalmic laser system according to an embodiment of the present invention.

FIG. 6 shows the geometric relation between the fast scan line 610 and the intended spherical dissection surface 620, e.g., of a lens, especially the distance deviation (δ) between the end point B of the scan line 610 and point A on the intended dissection surface 620. The maximum deviation δ is the distance between point A and point B, and is given by (Equation (1)):

$$\delta = \sqrt{R^2 + \frac{L^2}{4}} - R \approx \frac{L^2}{8R}$$

where R is greater than L. R is the radius of curvature of the surface dissection 620, and L is the length of the fast scan.

While the above maximum deviation analysis is for a spherical surface, this scanning method may also be used to create a smooth cut having a non-spherical shape, such as an ellipsoidal shape, etc. In such a case, the parallel of latitude and/or the meridian of longitude may not be circular.

In an exemplary case of myopic correction, the radius of curvature of the surface dissection may be determined by the amount of correction, ΔD, using the following equation (Equation (2)):

$$\Delta D = \frac{(n-1)}{R_1} + \frac{(n-1)}{R_2}$$

where n=1.376, which is the refractive index of cornea, and $R_1$ and $R_2$ (may also be referred herein as $R_t$ and $R_b$) are the radii of curvature for the top surface and bottom surface of a lenticular incision, respectively. For a lenticular incision with $R_1=R_2=R$ (the two dissection surface are equal for them to physically match and be in contact), we have (Equation (3)):

$$R = \frac{2(n-1)}{\Delta D}$$

FIG. 7 is a top view 950 of a lenticular incision 900 which illustrates three exemplary sweeps (1A to 1B), (2A to 2B) and (3A to 3B), with each sweep going through (i.e., going over) the lenticular incision apex 955. The incision diameter 957 ($D_{CUT}$) should be equal to or greater than the to-be-extracted lenticular incision diameter 917 (DL). A top view 980 shows the top view of one exemplary sweep.

Using such a "fast-scan-slow-sweep" scanning scheme, each sweep of the fast scan line forms a bent band, the bent band being the equivalent of bending a flat rectangle such that its long sides form arched shapes (the shape of the meridian of longitude) while its short sides remain straight. In the top view in FIG. 7 and FIG. 8B, the rectangular shapes represent the sweeps. In the central area of the lenticule cut, i.e. the area closer to the apex, multiple sweeps overlap each other. The amount of overlap decreases toward the edge of the lenticule cut. The inventors recognized that when the sweeping speed of each sweeps is constant, the central area experiences significant redundant cutting, causing unnecessary high energy deposit in this area. This is disadvantages because it may cause unnecessary cavitation bubbles which in turn may cause light scattering induced glare and halo. In particular, the high energy area is located at the center of the visual field, making it even more undesirable. Thus, preferred embodiments of the present invention alleviate this problem by speeding up the sweep in the central area of the lenticule. Moreover, speeding up the sweep in the central area will reduce the total amount of time require for producing the lenticule incisions.

Figure 8A:
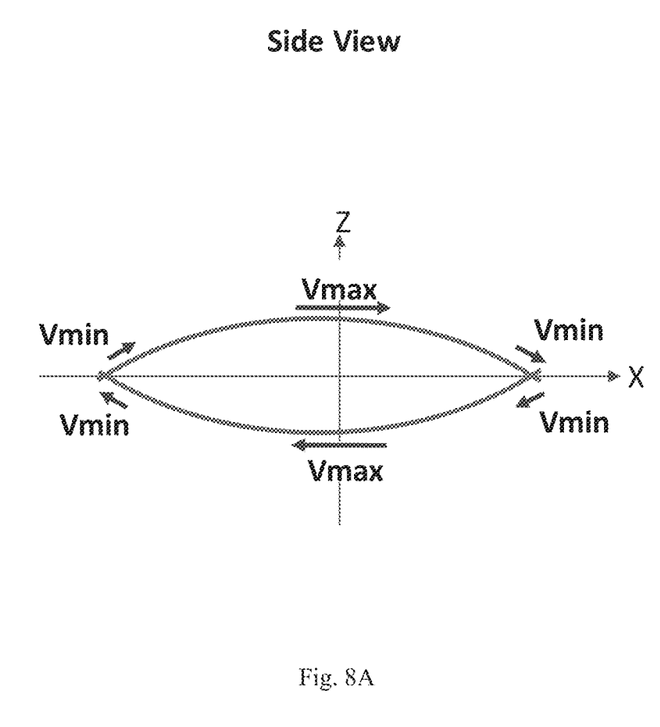
FIGS. 8A and 8B schematically illustrates a variable speed fast-scan-slow-sweep scheme of a surgical ophthalmic laser system according to an embodiment of the present invention.
Figure 8B:
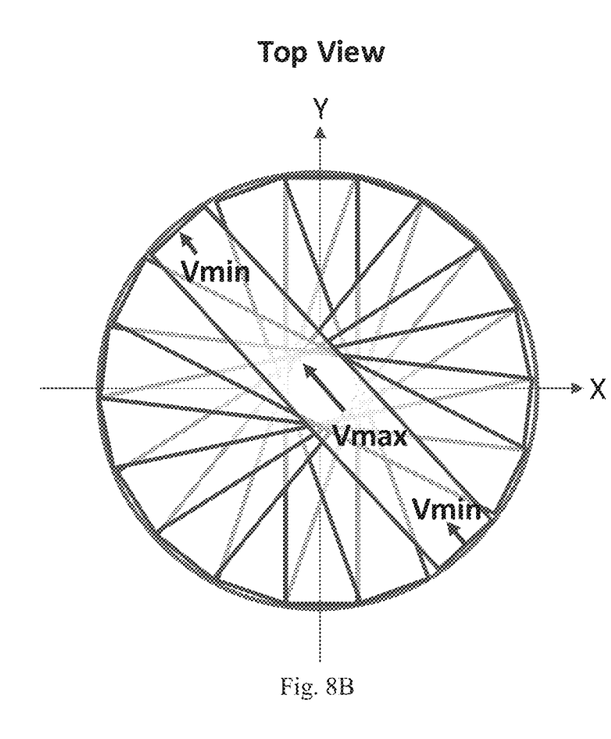

Therefore, in preferred embodiments of the present invention, the sweeping speed of each sweep is controlled to vary along the sweeping path (the meridian of longitude), with the speed being the highest in the areas near the apex (the midpoint of each sweep) where all sweeps overlap, and the lowest at the edge of the lenticule (the start and end portions of each sweep) where multiple sweeps have substantially no overlap, as schematically shown in FIGS. 8A (side view) and 8B (top view). The sweeping speed in the portions between the midpoint and the end points varies between the lowest and the highest speeds. The sweeping speed may vary in a continuous manner or in a stepwise manner.

Preferably, the lowest sweeping speed is determined by the required spatial density of the laser focal spots that is sufficient to form an incision surface that will result in tissue-bridge free separation of the tissue, such that a single sweep (i.e. no overlap with other sweeps) at the lowest sweeping speed will produce the required focal point density. The upper limit of the highest sweeping speed may be determined by the degree of overlap in the central area of the lenticule. If the scan pattern includes a total of N sweeps at different angles to form the entire lenticule, then in the central area having a diameter approximately equal to the width of the sweep, the upper limit of the highest sweeping speed may be N times the lowest speed, as all N sweeps will overlap in that area. In practice, the highest speed at the midpoint does not need to reach this upper speed limit, and a significant time reduction can still be achieved.

In a preferred embodiment, the sweeping speed is controlled according to the following equation (Equation (4)):

$$V(r) = V_{max} - \left(\frac{r}{R}\right)^2 * (V_{max} - V_{min})$$

where r is the radial position (i.e. the distance from the Z axis) of the fast scan line; R is the lateral radius of the lenticule; V(r) is the radial velocity (the sweeping speed) of the fast scan line as a function of the radial position r; $V_{max}$ is the maximum velocity (the highest sweeping speed) at the center of the lenticule, and $V_{min}$ is the minimum velocity (the lowest sweeping speed) at the edge of the lenticule.

Equation (4) is only an example; other suitable function for V(r) may be used. More generally, the variable sweeping speed is a first speed at the apex and a second speed at the edges, the first speed being higher than the second speed.

Figure 9:
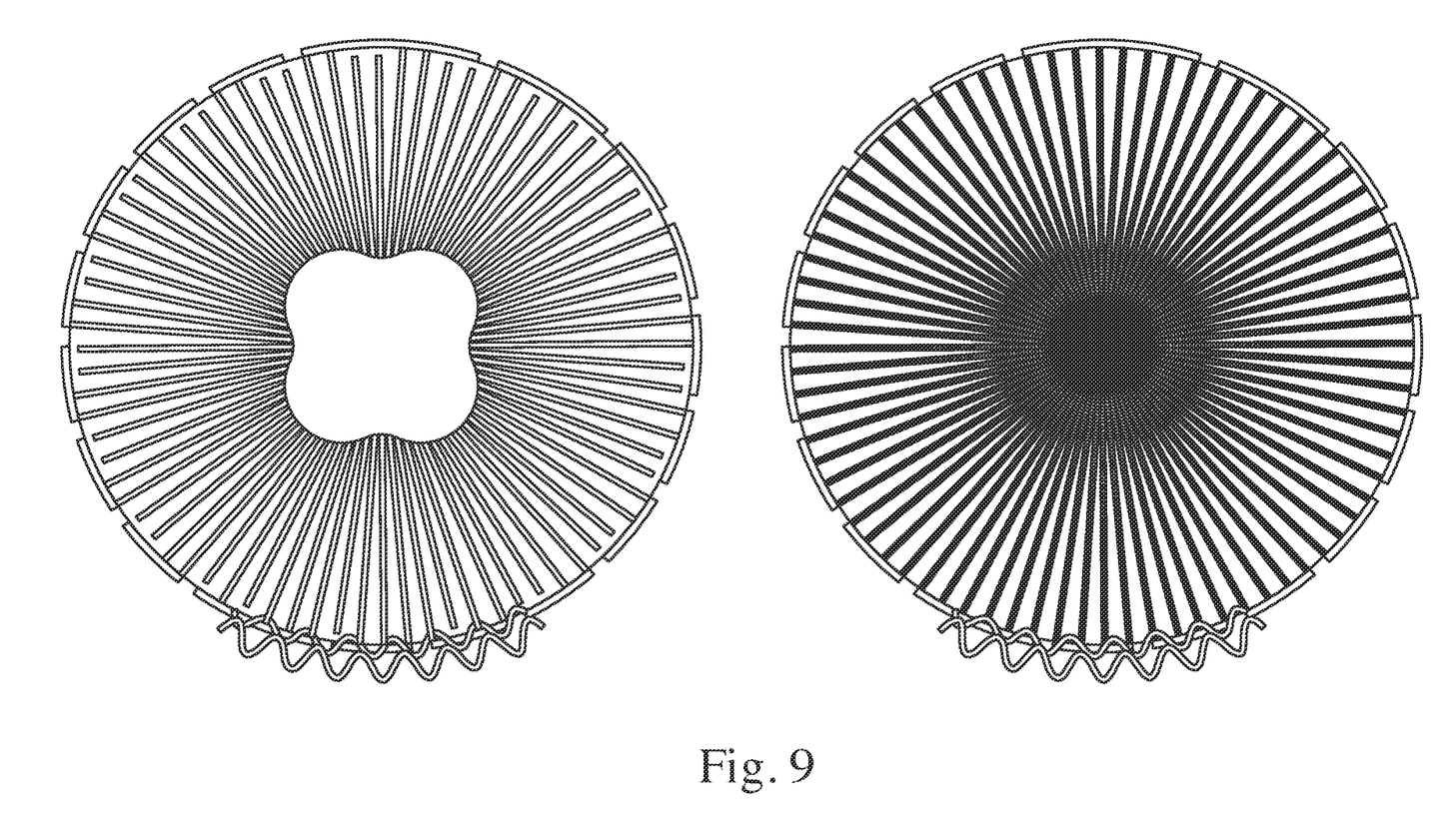
FIG. 9 show comparison of a constant speed fast-scan-slow-sweep scheme and variable speed fast-scan-slow-sweep scheme.

Using a variable sweeping speed, the total lenticule cutting time may be reduced by 50% or more as compared to using a constant sweeping speed equal to the lowest speed. In one example, using a variable sweeping speed according to the above Equation (4), with the lowest speed $V_{min}$ being 15 mm/s and the highest speed $V_{max}$ being 40 mm/s, the total cutting time was approximately 15 seconds. The laser pulse frequency was 10 MHz and the fast scan frequency of the resonant scanner was 8 kHz. In comparison, using a constant sweeping speed of 15 mm/s, with other parameters being equal, the total cutting time was approximately 30 seconds. Both cases achieved tissue-bridge free lenticule extraction. FIG. 9 shows a comparison of the cutting pattern (top view) for the constant speed sweeps (left) and variable speed sweeps (right). The laser spot density in the central area was significantly reduced.

The scanning method using variable sweeping speed allows optimizing the sweeping speed while keeping a substantially uniform distribution of laser focal spots across the lenticule surface, facilitating easy lenticule extraction.

In an embodiment, the lenticular incision is performed in the following steps:

1. Calculate the radius of curvature of the lenticule based on the amount of optical correction, e.g., using Equation (3) for a myopic correction.

2. Select the diameter for the lenticular incision to be extracted.

3. Select laser and optical system parameters, including the lowest sweeping speed $V_{min}$ and the highest sweeping speed $V_{max}$, and the sweeping speed as a function of radial position $V(r)$.

4. Perform the side incision first to provide a vent for gas that can be produced in the lenticular surface dissections. This is also the incision for the entry of forceps and for lens extraction.

5. Perform bottom surface dissection (the lower dissection as shown in side view of FIG. 8A). In doing so, the fast scan line is preferably kept tangential to the parallels of latitude, and the trajectory of the slow sweep drawn by X, Y, and Z scanning devices moves along the meridians of longitude near south pole in a sequence of 1A to 1B (first sweep of lenticular cut), 2A to 2B (second sweep of lenticular cut), 3A to 3B (third sweep of lenticular cut), and so on, using the sweeping speed $V(r)$ for each sweep, until the full bottom dissection surface is generated.

6. Perform the top surface dissection (the upper dissection as shown in the side view of FIG. 8A) in a similar manner as the bottom dissection is done. It is noted that the bottom dissection is done first. Otherwise, the bubble generated during the top dissection will block the laser beam in making the bottom dissection.

For illustrative purposes, in a myopic correction of $\Delta D=10$ diopter (i.e., 1/m), using equation (3), R=75.2 mm, which is indeed much greater than the length L of the fast scan. Assuming a reasonable scan line length of L=1 mm, using equation (1), the deviation $\delta$=1.7 μm. This deviation is thus very small. For comparison purpose, the depth of focus of a one micron (FWHM) spot size at 1 μm wavelength is about ±3 μm, meaning the length of focus is greater than the deviation $\delta$.

Figure 10:
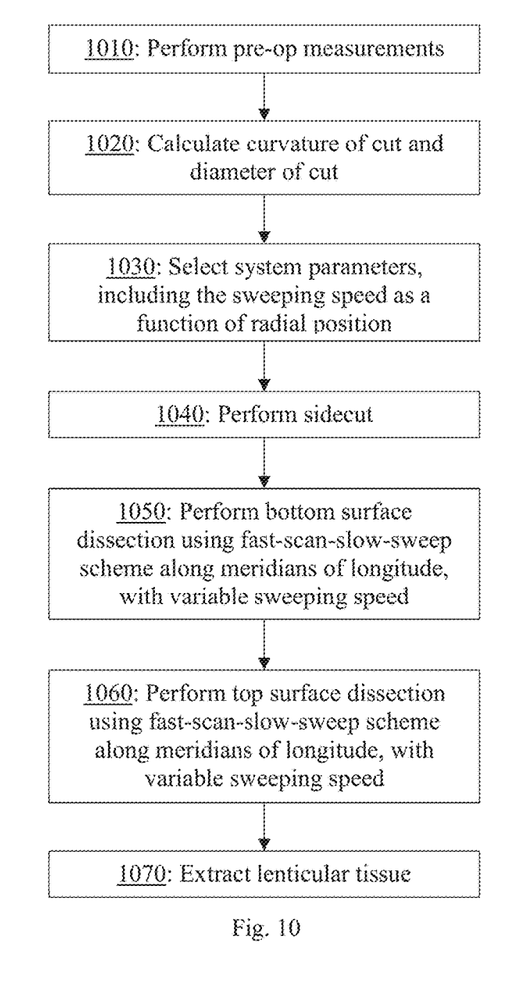
FIG. 10 is a flowchart illustrating a process according to an embodiment of the present invention.

FIG. 10 illustrates a process of the laser system 10 according to an embodiment. The laser system 10 may start a surgical procedure performing pre-operation measurements (Action Block 1010). For example, in an ophthalmologic surgery for myopic correction, the myopic diopter is determined, the reference depth position is determined, and so on. The laser system 10 calculates the radius of curvature based on the amount of correction, e.g., the myopic correction determined in pre-operation measurements, as shown, for example, in equations (2) and (3) above, and calculates the diameter of the incision, as shown by $D_{CUT}$ in FIG. 7 (Action Block 1020). $D_{CUT}$ is equal to or greater than the diameter of the to-be-extracted lenticule (DL in FIG. 7). The system select various laser and optical system parameters, including the sweeping speed as a function of radial position $V(r)$ along with the parameters $V_{min}$ and $V_{max}$ (Action Block 1030).

The laser system 10 first performs side incision to provide a vent for gas that can be produced in the lenticular surface dissections, and for tissue extraction later on (Action Block 1040). The laser system 10 then performs the bottom lenticular surface dissection (Action Block 1050) before performing the top lenticular surface dissection (Action Block 1060). The bottom and top lenticular surface dissection are performed using a fast-scan-slow-sweep scheme along the meridians of longitude, with variably sweeping speed, as described above. The lenticular tissue is then extracted (Action Block 1070).

The variable sweeping speed method according to embodiments of the present invention has many advantages over the conventional constant sweeping speed method. It avoids redundant cutting, which reduces unnecessary cavitation bubbles, particularly at the center of the visual field, and thus reduces light scattering-induced glare and halo in the patient's eye. It reduces the time of the lenticular incision procedure (e.g. by 50%) without compromising the tissue-bridge free incision quality. Advantages of reduced procedure time includes: reduced patient discomfort during eye docking (docking refers to physically coupling the patient's eye to the laser system optics using a patient interface device); reduced risk of incision failure due to insecure coupling of the patient interface device to the eye (for example, when a patient interface uses suction force to couple the patient interface to the eye surface, suction loss may cause failure of the coupling); reduced risk of damage to the sclera due to long applanation (the flattening of the cornea by the patient interface device) and suction; and reduced risk of damage to retina due to high intraocular pressure during docking.

The above described embodiments solve the problem of redundant energy deposit near the central area by increasing the sweeping speed near the central area. In alternative embodiments of the present invention, this problem may be solved by varying other parameters of the laser system, including: controlling the laser device to dynamically reduce the laser pulse energy when the scan line is located in a central area of the lenticule (e.g. an area having a diameter approximately equal to the width of the sweep) during the sweep as compared to when the scan line is located near the edge of the lenticule; increasing the width of the fast scan line, without changing the number of pulses per scan line (that is a function of the laser), so that the energy density (total energy per area) is reduced. All of these methods reduce the energy density near the center of the field of view.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. An ophthalmic surgical laser system comprising:
    a laser delivery system for delivering a pulsed laser beam to a target in a subject's eye;
    a high frequency scanner to scan the pulsed laser beam back and forth at a predefined frequency;
    an XY-scanner to deflect the pulsed laser beam, the XY-scanner being separate from the high frequency scanner;
    a Z-scanner to modify a depth of a focus of the pulsed laser beam; and
    a controller configured to control the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, wherein each sweep is formed by:
        controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex,
        controlling the XY-scanner and the Z-scanner to move the scan line along a meridian of longitude of the lens, the meridian of longitude being a curve that passes through the apex and has a defined angular position around the Z axis, and
        controlling the laser delivery system to vary a laser pulse energy during each sweep to use a lower laser pulse energy when the scan line is located within a vicinity of the apex of the lenticule than when the scan line is located at an edge of the lenticule,
    wherein the plurality of sweeps are successively formed one after another along the respective meridians of longitude which are different from one another.

2. The ophthalmic surgical laser system of claim 1, wherein the high frequency scanner is a resonant scanner.

3. The ophthalmic surgical laser system of claim 1, wherein the predetermined length of the scan lines for all sweeps are equal.

4. The ophthalmic surgical laser system of claim 1, wherein the predetermined length of the scan line for each sweeps is between 0.9 mm and 1.1 mm, and wherein the high frequency scanner has a scanning frequency between 7 kHz and 9 kHz.

5. The ophthalmic surgical laser system of claim 1, further comprising a prism disposed to receive scanned pulsed laser beam from the high frequency scanner, and wherein the controller is configured to rotate the prism to rotate an orientation of the scan line.

6. The ophthalmic surgical laser system of claim 1, wherein the at least one lenticular incision includes a top lenticular incision and a bottom lenticular incision, wherein the curved surface is a top surface of the lens corresponding to the top lenticular incision, the lens further including a bottom surface corresponding to the bottom lenticular incision and defining another apex, and wherein the scan line for each of the sweeps forming the top lenticular incision is moved over the top surface of the lens through the apex of the top surface of the lens, and the scan line for each of the sweeps forming the bottom lenticular incision is moved over the bottom surface of the lens through the other apex of the bottom surface of the lens.

7. The ophthalmic surgical laser system of claim 1, wherein a deviation exists between an end point of the scan line and a point on the surface of the lens which is a spherical surface, the deviation being $$\delta = \sqrt{R^2 + \frac{L^2}{4}} - R \approx \frac{L^2}{8R}$$

where R is a radius of curvature of the spherical surface of the lens, and L is the length of the scan line.

8. The ophthalmic surgical laser system of claim 7, wherein a depth of a focus of the pulsed laser beam is calculated based on the radius of curvature of the spherical surface of the lens.

9. A method for creating a lenticular incision using an ophthalmic surgical laser system, the method comprising the steps of:
    generating a pulsed laser beam;
    delivering the pulsed laser beam to a target in a subject's eye;
    scanning, by a high frequency scanner, the pulsed laser beam back and forth at a predefined frequency;
    deflecting, by an XY-scanner, the pulsed laser beam, the XY-scanner being separate from the high frequency scanner;
    modifying, by a Z-scanner, a depth of a focus of the pulsed laser beam; and
    controlling, by a controller, the high frequency scanner, the XY-scanner and the Z-scanner to successively form a plurality of sweeps which collectively form at least one lenticular incision of a lens in the subject's eye, the lens having a curved surface that defines an apex and a Z axis passing through the apex, including forming each sweep by:
        controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the Z axis and has a defined distance to the apex,
        controlling the XY-scanner and the Z-scanner to move the scan line along a meridian of longitude of the lens, the meridian of longitude being a curve that passes through the apex and has a defined angular position around the Z axis, and
        controlling the laser delivery system to vary a laser pulse energy during each sweep to use a lower laser pulse energy when the scan line is located within a vicinity of the apex of the lenticule than when the scan line is located at an edge of the lenticule, wherein the plurality of sweeps are successively formed one after another along the respective meridians of longitude which are different from one another.

10. The method of claim 9, wherein the predetermined length of the scan lines for all sweeps are equal.

11. The method of claim 9, wherein the predetermined length of the scan line for each sweeps is between 0.9 mm and 1.1 mm, and wherein the high frequency scanner has a scanning frequency between 7 kHz and 9 kHz.

12. The method of claim 9, further comprising: controlling, by the controller, a rotation of a prism which is disposed to receive scanned pulsed laser beam from the high frequency scanner to rotate an orientation of the scan line.

13. The method of claim 9, wherein the at least one lenticular incision includes a top lenticular incision and a bottom lenticular incision, wherein the curved surface is a top surface of the lens corresponding to the top lenticular incision, the lens further including a bottom surface corresponding to the bottom lenticular incision and defining another apex, and wherein the scan line for each of the sweeps forming the top lenticular incision is moved over the top surface of the lens through the apex of the top surface of the lens, and the scan line for each of the sweeps forming the bottom lenticular incision is moved over the bottom surface of the lens through the other apex of the bottom surface of the lens.

14. The method of claim 9, wherein a deviation exists between an end point of the scan line and a point on the surface of the lens which is a spherical surface, the deviation being $$\delta = \sqrt{R^2 + \frac{L^2}{4}} - R \approx \frac{L^2}{8R}$$

where R is a radius of curvature of the spherical surface of the lens, and L is the length of the scan line.

15. The method of claim 14, wherein a depth of a focus of the pulsed laser beam is calculated based on the radius of curvature of the spherical surface of the lens.

* * * * *